(12) United States Patent
Marckmann et al.

(10) Patent No.: US 10,968,191 B2
(45) Date of Patent: *Apr. 6, 2021

(54) ENERGY-EFFICIENT AND ENVIRONMENTALLY FRIENDLY PROCESS FOR THE PRODUCTION OF TARGET CHEMICAL COMPOUNDS FROM CELLULOSIC MATERIAL

(71) Applicant: CLARIANT INTERNATIONAL LTD., Muttenz (CH)

(72) Inventors: Henning Marckmann, Buchloe (DE); Ralf Hortsch, Munich (DE); Marco Schuth, Altdorf (DE); Bernhard Arzt, Kandel (DE)

(73) Assignee: Clariant International Ltd., Muttenz (CH)

( * ) Notice: Subject to any disclaimer, the term of this patent is extended or adjusted under 35 U.S.C. 154(b) by 0 days.

This patent is subject to a terminal disclaimer.

(21) Appl. No.: 16/273,619

(22) Filed: Feb. 12, 2019

(65) Prior Publication Data

US 2019/0177292 A1 Jun. 13, 2019

Related U.S. Application Data

(63) Continuation of application No. 15/501,482, filed as application No. PCT/EP2015/067573 on Jul. 30, 2015, now Pat. No. 10,202,358.

(30) Foreign Application Priority Data

Aug. 6, 2014 (EP) .................................... 14002758

(51) Int. Cl.
*C07D 307/50* (2006.01)
*C08H 8/00* (2010.01)
*C07C 45/55* (2006.01)
*C07C 51/31* (2006.01)
*B01D 11/02* (2006.01)
*B01J 20/18* (2006.01)

(52) U.S. Cl.
CPC ........ *C07D 307/50* (2013.01); *B01D 11/0223* (2013.01); *B01D 11/0292* (2013.01); *B01J 20/18* (2013.01); *C07C 45/55* (2013.01); *C07C 51/31* (2013.01); *C08H 8/00* (2013.01)

(58) Field of Classification Search
CPC ................................................... C07D 307/50
See application file for complete search history.

(56) References Cited

U.S. PATENT DOCUMENTS 4,136,207 A * 1/1979 Bender .................. A23K 10/32
162/18
10,202,358 B2 * 2/2019 Marckmann ............ C08H 8/00

FOREIGN PATENT DOCUMENTS

| CN | 103214439 A | 7/2013 | |
|---|---|---|---|
| EP | 2134850 A1 | 12/2009 | |
| EP | 2471940 A1 | 7/2012 | |
| EP | 2623607 A1 | 8/2013 | |
| WO | 2010121367 A1 | 10/2010 | |
| WO | 2010151536 A1 | 12/2010 | |
| WO | WO-2010151536 A1 * | 12/2010 | ......... C08B 37/0003 |
| WO | 2011093635 A2 | 8/2011 | |

* cited by examiner

*Primary Examiner* — John S Kenyon
(74) *Attorney, Agent, or Firm* — Verrill Dana, LLP

(57) ABSTRACT

The present invention is directed to an energy-efficient and environmentally friendly process for the production of chemical target compounds from cellulosic material. In a further aspect, the present invention is directed to a system for conducting the process according to the inventive process.

9 Claims, 4 Drawing Sheets

ENERGY-EFFICIENT AND ENVIRONMENTALLY FRIENDLY PROCESS FOR THE PRODUCTION OF TARGET CHEMICAL COMPOUNDS FROM CELLULOSIC MATERIAL

CROSS REFERENCE TO RELATED APPLICATIONS

This application is a continuation of U.S. application Ser. No. 15/501,482, filed 3 Feb. 2017, which is the national phase of PCT/EP2015/067573, filed 30 Jul. 2015, which claims priority to European Patent Application No. 14002758.2, filed on 6 Aug. 2014. The entire contents of each of the aforementioned applications are hereby incorporated by reference.

BACKGROUND

Due to limited resources of mineral oil and demands to reduce $CO_2$ emissions the chemical industry seeks more sustainable production routes for the manufacture of commodity chemicals such as liquid fuels and base chemicals. Part of that strategy focusses on the conversion of cellulosic biomass into versatile chemicals or fuels such as ethanol. Lignocellulosic biomass contains cellulose (~25-40% w/w d.s.), hemicellulose (~15-25% w/w d.s.) and lignin (~15-30% w/w d.s.) as major components and minor amounts of other carbohydrates, waxes, proteins and inorganic compounds. Among forms of plant biomass, lignocellulosic biomass derived from any forestry and agricultural waste streams, such as wood residues and cereal straw are particularly well suited for conversion to commodity chemicals and fuels because of their availability, low cost and environmentally sound production. Additionally, life cycle analyses of production processes utilising lignocellulosic feedstocks indicate reduced greenhouse gas emissions compared to processes based on other feedstocks.

Exemplary unit operations for e.g. the biotechnological conversion of lignocellulosic material (e.g. straw) to value-adding products (e.g. ethanol) are: mechanical de-sizing and/or physicochemical pretreatment, enzymatic hydrolysis, fermentation and product recovery. To ascertain maximum process efficiency it is mandatory to convert a maximum amount of polysaccharides into soluble sugars during the enzymatic hydrolysis unit.

Various process options that describe the conversion of lignocellulosic biomass to ethanol and other base chemicals have been described within the state of the art. The EP 2 623 607 A1 discloses a process for the production of e.g. ethanol from cellulosic biomass wherein the flash steam from the high pressure pre-treatment of the cellulosic material is reused within the distillation of the ethanol (product recovery).

To realize these processes on an industrial scale it is particularly desirable to transfer the maximal amount of energy, carbon and mass content contained in the renewable feedstock to the desired end products. Further, according to the upcoming awareness of environmental issues, cleaner production methods are in great demand. At present none of the described conversion processes have realised this to a satisfactory extent.

Thus, there is a need for further processes for the conversion of biomass material to chemical target compounds which do not show these deficits.

SUMMARY

The present invention is directed to an energy-efficient and environmentally friendly process for the production of target chemical compounds from cellulosic material. In a further aspect, the present invention is directed to a system for conducting the process according to the inventive process.

DETAILED DESCRIPTION

Figure 1:
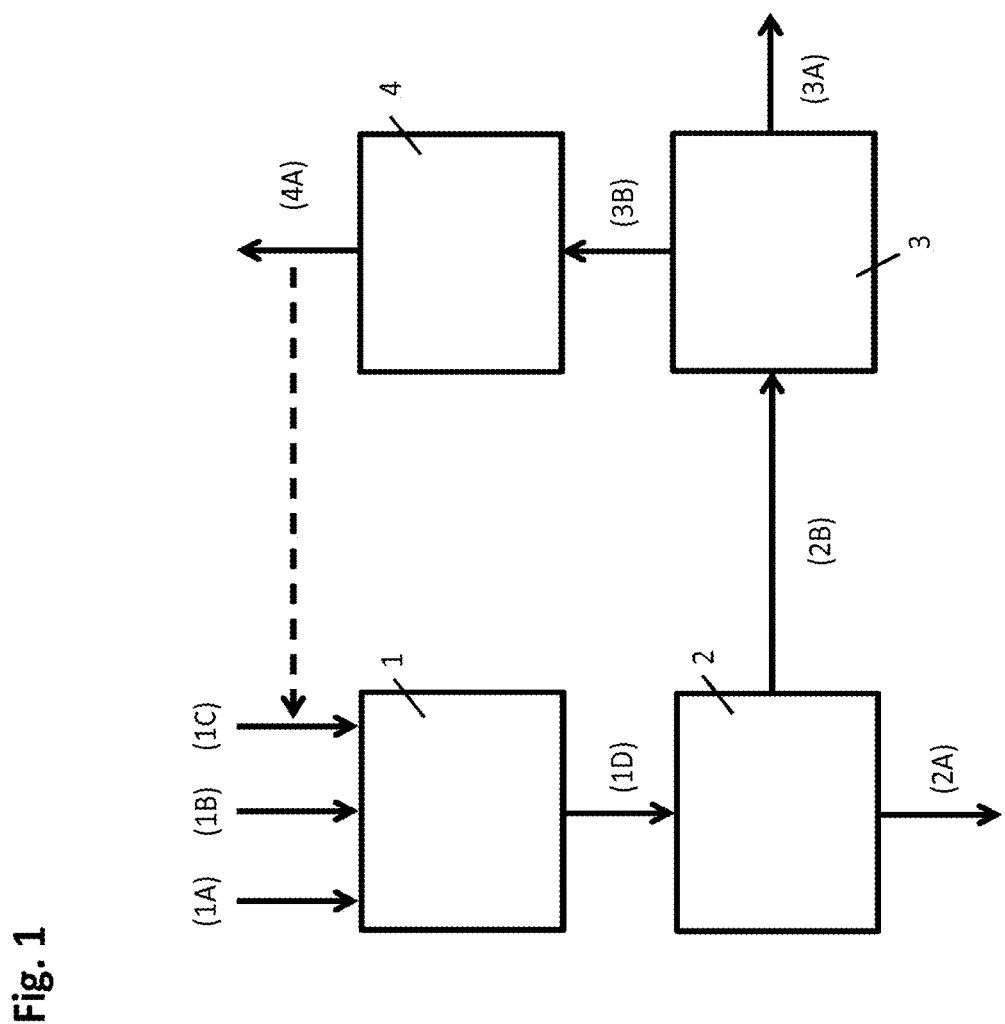
FIG. 1 illustrates a typical system for carrying out the process of the present invention wherein the treatment reactor (1) is fed by three process streams, the stream containing the cellulosic material (1A), the stream containing steam (1B) and the stream containing process water (1C) which may be recycled steam condensate from the steam usage device (4). The steam-containing treated cellulosic material is then transferred by another process stream (1D) to a steam separation device (2). Two process streams emerge from the steam separation device (2), the stream of treated cellulosic material (2A) and the stream containing steam and the at least one chemical target compound (2B). The stream containing the at least one chemical target compound (2B) is then transferred to a steam segregation device (3). Two process streams emerge from the steam segregation device (3), the stream containing the at least one chemical target compound (3A) and the stream containing the remaining purified steam (3B). The stream containing the remaining purified steam (3B) is then further transferred to a steam utilization device (4) and from the steam utilization device (4), the condensed steam (4A) is recycled to the treatment reactor (1) to be used as process water.

The inventors of the present invention have now surprisingly discovered that these deficits can be overcome by a process for the production of chemical target compounds from cellulosic material comprising the steps
 a) treating the cellulosic material by applying steam;
 b) separating the steam containing at least one chemical target compound from the treated cellulosic material;
 c) transferring the separated steam to a segregation device;
 d) segregating the phase containing the least one chemical target compound from the steam;
 e) subjecting the steam to a utilization step.

The process for the production of chemical target compounds from cellulosic material of the present invention is particularly advantageous as it is highly efficient as one or more chemical target compounds can be produced from the starting material: e.g. the (pre)treated cellulosic material may be further processed according to a bioethanol production process. In addition, one or more different compounds can be segregated from the steam. The production of chemical compounds from cellulosic material according to the present invention is also highly profitable as steam from the pre-treatment of the cellulosic material is reused in form of steam-energy which can be transferred to various other applications within or outside the actual production process but also in form of process water after re-use and/or condensation contributing to substantial savings of production cost.

Within the present invention the term "cellulosic material" is to be understood as to comprise all kind of material known to a person skilled in the art as comprising cellulose, hemicellulose or lignocellulose. Preferably, the "cellulosic material" is selected from "lignocellulosic material".

Within the present invention "lignocellulosic material" is to be understood to comprise all kind of material known to a person skilled in the art as comprising lignocellulose. Terms "lignocellulose-containing material", "lignocellulose-containing biomass", "lignocellulosic material" and "lignocellulosic biomass" are to be understood as synonyms within the present invention. Particularly preferred lignocellulosic materials according to the present invention include wood, cereal straw and/or husks, corn stover, bagasse, oat hulls, switch grass, cellulose, raw paper pulp (obtained from pulp and paper production) and mixtures thereof. Alternative sources or additional components may comprise one or more of the following components: purified cellulose, pulp, milk whey, molasses or sugars such as glucose and lactose. In a preferred embodiment the lignocellulosic material contains at least 25 wt.-%, preferably at least 40 wt.-%, more preferred at least 70 wt.-%, even more preferred at least 80 wt.-% and most preferred at least 90 wt.-% lignocellulose. It is to be understood that the lignocellulosic material may also comprise other compounds such as proteinaceous material, starch, sugars, such as fermentable sugars and/or non-fermentable sugars.

Within the present invention the term "treatment of the cellulosic material by applying steam" is to be understood as any kind of application of steam known to a person skilled in the art as suitable for the inventive process and can be in combination with any kind of mechanical, biological, chemical and/or physical treatment methods known to a person skilled in the art as suitable for the inventive process. Within a preferred embodiment, the treatment of cellulosic material is carried out by applying steam under elevated pressure and is more preferably carried out as "steam explosion". If lignocellulosic material is used within the process according to the invention the application of steam leads to at least partial removal and separation of hemicellulose from cellulose and disruption and removal of the lignin sheath in order to decrease the crystallinity of cellulose and thus to increase the accessible surface area of cellulose and/or to increase the pore size of cellulose.

"Steam explosion" according to the present invention preferably comprises a pressurised hydrothermal treatment at a temperature of from 60 to 350° C., preferably from 80 to 300° C., particularly preferred from 120 to 250° C. and most preferred from 150 to 220° C. of the lignocellulose-containing material in the absence or presence of acidic (such as $H_2SO_4$, HCl, $H_3PO_4$) or base/alkaline (such as $NH_4OH$, NaOH, KOH, lime) catalysts, which are added at concentrations from 0.01 to 15% (wt./wt.), preferably from 0.05 to 12.5% (wt./wt.), more preferred from 0.1 to 10% (wt./wt.) and most preferred from 0.25 to 7.5% (wt./wt.). In a preferred embodiment of the present invention the pressure is preferably selected from 1 to 100 bar, preferably from 2 to 50 bar, also preferred from 3 to 25 bar and most preferred from 5 to 15 bar. Reaction times during steam explosion have to be selected from 10 s to 2 h, preferably from 1 minute to 1.5 hours, and most preferred from 5 minutes to 1 hour. Choosing the parameters within these preferred conditions guarantees efficient transformation of the biomass components and leads to an ideal starting material for e.g. subsequent enzymatic hydrolysis of a bioethanol production process. Within a particularly preferred embodiment a "mechanical comminution" treatment of the cellulosic material is carried out before or during the steam explosion treatment, wherein the mechanical comminution is selected from the group consisting of mechanical processing, grinding, chopping, crushing, cutting, irradiation, milling and combinations thereof.

Treatment methods suitable for the process of the present invention are to be carried out within suitable devices known to a person skilled in the art. A device suitable for carrying out steam explosion may be any kind of vessel such as a batch reactor but may also be carried out within a screw reactor, preferably a continuous screw reactor.

In a preferred embodiment the solids content of the treated cellulosic material is up to 75% (wt./wt.), preferably from 25 to 65% (wt./wt.) and particularly preferred from 40 to 55% (wt./wt.).

Separating the steam containing at least one chemical target compound according to step b) of the inventive process may be carried out by any device and/or method known to a person skilled in the art as suitable for the inventive process. Within a preferred embodiment of the process, the separation of the steam is carried out by use of a steam separation device, such as a pressure-cyclone or a mechanical solid-gas separation device ("Mechanical steam separator"). Separation at an elevated pressure level guarantees efficient separation of volatile products and a more energy-efficient use of the steam in other process steps. In a pressure cyclone the material is separated gravimetrically by introducing the solids-containing steam tangentially into a cyclone. The pressure is preferably selected from 2 to 10 bar, particularly preferred 3 to 8 bar and most preferred 4.5 to 5.5 bar. Due to the different densities the steam leaves the cyclone at the top and the solids at the bottom. The mechanical solid-gas separation device operates with rotating turbines where solid particles are accumulated whereas the gaseous steam phase leaves the device at the top due to the different densities. With this system a minimum carry-over of solids in the steam phase is guaranteed.

After separating the steam from the treated cellulosic material, the so pre-treated cellulosic material may be further transferred to another vessel and undergo a saccharification process and/or use as e.g. raw material within a bioethanol production process. Suitable processes for saccharification are known within the art. A particularly suitable process is disclosed within the EP 2 471 940 and the EP 2 134 850 which have been developed by the applicant and are herein incorporated by reference.

Steam used within a treatment according to step a) of the inventive process which has been defined above may contain one or more of the following chemical compounds:

Phenolic compounds, furans, 4-OH benzyl alcohol, 4-OH benzaldehyde, 4-OH benzoic acid, trimethyl benzaldehyde, 2-furoic acid, coumaric acid, ferulic acid, phenol, guaiacol, veratrole, pyrogallol, pyrogallol mono methyl ether, vanillyl alcohol, vanillin, isovanillin, vanillic acid, isovanillic acid, homovanillic acid, veratryl alcohol, veratraldehyde, veratric acid, 2-O-methyl gallic acid, syringyl alcohol, syringaldehyde, syringic acid, trimethyl gallic acid, homocatechol, ethyl vanillin, creosol, p-methyl anisol, anisaldehyde, anisic acid, furfural, hydroxymethylfurfural, 5-hydroxymethylfurfural, formic acid, acetic acid, levulinic acid, cinnamic acid, coniferyl aldehyde, isoeugenol, hydroquinone and eugenol.

Many of these compounds are inhibitory or even toxic for further possible applications of the steam and/or process water but also constitute valuable target chemicals such as furfural, hydroxymethylfurfural, 5-hydroxymethylfurfural or organic acids such as acetic acid.

According to step c) of the process of the present invention, the steam separated from the treated cellulosic material is therefore transferred to a segregation device to segregate and accumulate one ore more of these compounds. Within or by use of the segregation device the phase containing the at least one chemical target compound and the watery steam are segregated.

The transfer can be accomplished by any method known to a person skilled in the art as suitable for the inventive process and is preferably carried out by pipings.

The segregating according to step d) of the inventive process can be carried out by any method known to a person skilled in the art as suitable for the inventive process. The segregation is preferably carried out by use of a segregation device. Within a particularly preferred embodiment, the segregation device preferably comprises a rectification device (such as a rectification column) or adsorption column or a gas-permeation membrane. In embodiments of the present invention wherein the segregation device comprises more than one component (such as e.g. a rectification device, an adsorption column or a gas-permeation membrane) these components are referred to as "segments". The rectification device (or adsorption column or a gas-permeation membrane) is then referred to as "first segment".

The rectification column (fractionating column, fractionation column, fractional column—all terms are used synonymously within the present invention)—which is preferably used as first segment of the segregation device within the process according to the present invention enables the segregation of compounds with close volatility.

In a typical rectification device which is suitable for the inventive process, steam containing the chemical target compound(s) rises up the column. The steam condenses on e.g. glass spurs (such as trays or plates) inside the column, and returns to a distilling flask, refluxing the rising distillate steam. The hottest tray is at the bottom of the column and the coolest tray is at the top. At steady-state conditions, the steam and liquid on each tray reach equilibrium. Only the most volatile of the chemical (target) compound stays in gas form all the way to the top, where it may then proceed through a condenser, which cools the gaseous chemical target compound until it condenses into a liquid distillate. The separation may be enhanced by the addition of more trays (to a practical limitation of heat, flow, etc.). Within a preferred embodiment, the rectification column comprises from 1 to 100, preferably from 5 to 80, further preferred from 10 to 60 and most preferred from 15 to 30 plates or trays which are further preferred manufactured from stainless steel, ceramic materials or plastics. The temperature within the rectification column is preferably chosen from 110 to 180° C., preferably from 120 to 160° C. and most preferred from 125 to 140° C. The pressure within the rectification column is preferably selected from 1 to 6.5 bar, preferably from 2 to 5 bar and most preferred from 3 to 4 bar. Within another preferred embodiment the rectification column is manufactured as a packed column comprising 1 to 50 packet sections, preferably 2 to 20 packet sections, further preferred 2 to 10 packet sections.

The segregation according to step d) of the inventive process may also be carried out by use of an adsorption column. Suitable adsorbers to be used within the column may be selected from zeolites such as beta- or MFI-zeolites, silicalites, silica, bentonite, silicalite, clay, hydrotalcite, alumo-silicalite, aluminate, clinoptolite, gismondine, activated carbon, montmorillonite, organic polymers, polytetrafluoroethylen (PTFE, Teflon) and mixtures thereof.

The segregation according to step d) of the inventive process may also be carried out by use of a gas-permeation membrane.

The use of a rectification column is thereby preferred as the steam energy is mainly unaffected and can be re-used within further applications.

Within a particularly preferred embodiment, the segregation device further comprises a steam transformer as second segment for condensation and further purification of the respective phase and particular chemical target compound. Such steam transformers may be selected from falling-film evaporators, heat exchangers, plate heat exchangers, forced circulation steam evaporators. The use of a steam transformer within the segregation device is thereby particularly preferred as the steam will be condensed which enables easy separation of the at least one chemical target compound.

Within a further particularly preferred embodiment, the segregation device further comprises a decanter as third segment which further improves the separation of the at least one chemical target compound and remaining watery phase. Suitable decanters may be selected from mechanical decanters, centrifuges, decantation vessels, adsorption devices, chromatography devices, further rectification devices and distillation devices, whereas decantation vessels are particularly preferred.

Within a particularly preferred embodiment of the process according to the present invention, the condensed and/or decanted watery phase (in the following "residual phase") is then (re-) transferred to the first segment of the segregation device, e.g. the rectification column or adsorption column. By transferring the residual phase back to the first segment of the segregation device, further minor amounts of chemical target compounds may be segregated within a second or third cycle of segregation (such as rectification or adsorption) leading to a further improvement of efficiency and profitability of the process.

Within a further preferred embodiment of the inventive process, the utilization step e) is selected from evaporation, drying and distillation heating, sterilisation of vessels, generating electricity by a turbine or a nozzle. Thus, the steam is transferred from the segregation device to a further application such as evaporation, drying and distillation which may be part of e.g. a parallel saccharification process of the treated cellulosic material or part of a parallel bioethanol production process as outlined before. Regarding the utilization of the steam within a bioethanol production process, according to a particular preferred embodiment, the steam may be transferred to a drying device for drying of the lignin-containing waste fraction of a bioethanol process or transferred to a distillation device for recovery of the produced alcohol of a bioethanol process.

Within step e), the utilized steam is either condensed automatically by the respective application or can be transferred to a separate condenser according to step f) of the inventive process. The condensed steam may then be further recycled as process water within the inventive or other processes and is preferably transferred to the treatment of the cellulosic material according to step a) of the inventive process. As the steam has been depleted by toxic and/or inhibitory compounds such as furfural, the condensed steam is suitable for many further applications and may also be used as process water within the hydrolysis or fermentation step of a saccharification or bioethanol production process. Within a preferred embodiment, the condensed steam is used as process water and recycled to the treatment reactor. The process according to the present invention comprises preferably a further step g) recycling of the condensed steam of step f) to step a) of the process.

Within another aspect of the present invention, the utilization of the steam energy may also be carried out before the segregation of the phase containing the at least one chemical target compound. The respective process variant comprises the steps
a) treating the cellulosic material by applying steam;
b) separating the steam containing at least one chemical target compound from the treated cellulosic material;
b1) subjecting the separated steam to a utilization step;
c1) transferring the stream of the utilized steam to a segregation device;
d1) segregating the phase containing the at least one chemical target compound from the stream of the utilized steam;
g1) recycling of the stream of step d1).

Steps a), and b) are thereby carried out according to the definitions and preferred embodiments as described before.

Step b1) is thereby carried out according to the definitions and preferred embodiments as described before regarding step e). It is thereby particularly preferred that the utilization of the separated steam will automatically involve condensation of the steam. In case the utilization will not lead to a condensation of the steam, within a preferred embodiment of the respective process variant, the steam will be transferred to a condenser before step c1).

The condensed steam (stream of the utilized steam) is then transferred to a segregation device according to step c1). Step c1) is thereby carried out according to the definitions and preferred embodiments as described before regarding step c).

Step d1) is thereby carried out according to the definitions and preferred embodiments as described before regarding step d). In addition, segregation of the at least one chemical target compound may be carried out by filtration such as nanofiltration or pervaporation by use of e.g. a polydimethylsiloxane (PDMS), silicone, polyurethaneurea (PUU) membrane or washing of the stream.

Step g1) is thereby carried out according to the definitions and preferred embodiments as described before regarding the recycling of the condensed steam according to step g). The condensed steam or stream according to step d1) is suitable for many further applications and may also be used as process water within the hydrolysis or fermentation step of a saccharification or bioethanol production process. Within a preferred embodiment, the stream according to step d1) is used as process water and recycled to the treatment reactor according to step g) as described before.

Within another aspect, the present invention is directed to a system for conducting the process for the production of chemical target compounds from cellulosic material as defined before comprising
(i) reactor for the treatment of the cellulosic material according to step a) of the inventive process;
(ii) steam separation device for separating the steam containing at least one chemical target compound from the treated cellulosic material according to step b) of the inventive process;
(iii) steam segregation device for segregating the phase containing the least one chemical target compound from the steam according to step d) or d1) of the inventive process;
(iv) steam utilization device for steam energy utilization.

The reactor (i) can be any reactor known to a person skilled in the art as suitable for the inventive system and is preferably selected from a batch reactor, a screw reactor, preferably a continuous screw reactor.

Within a particularly preferred embodiment, the segregation device preferably comprises a rectification device (such as a rectification column) or adsorption column or filtration membrane or pervaporation membrane or gas-permeation membrane. In embodiments of the present invention wherein the segregation device comprises more than one component (such as e.g. a rectification device) these components are referred to as "segments". The e.g. rectification device is then referred to as "first segment". It is thereby particularly preferred that the segregation device comprises a rectification device as a first segment.

Within another preferred embodiment of the inventive system, the segregation device further comprises a steam transformer as second segment for condensation and further purification of the respective phase and particular chemical target compound. Within another preferred embodiment, the segregation device further comprises a decanter as a third segment for condensing the utilised steam. The decanter can be any device known to a person skilled in the art as suitable for the inventive system and is preferably selected from mechanical decanters, centrifuges, decantation vessels, adsorption devices, chromatography devices, further rectification devices, distillation devices, whereas decantation vessels are particularly preferred. The first, second and/or third segment may be arranged within one unit or may also be arranged one after the other. Within a particularly preferred embodiment, the segregation device (iii) comprises three (first, second and third) segments which are arranged one after the other.

Within another preferred embodiment, the inventive system further comprises a condenser (v) which is preferably located after the steam transformer and condenses the steam coming from the steam utilization device (iv). Systems comprising a condenser are preferred within application wherein the steam utilization device (iv) will not emit already condensed steam or wherein the utilization of the steam within step e) of the inventive process will not involve condensation. The condensation of the utilized steam— either automatically or by a condenser—is particularly preferred as the so obtained water may be even further used as process water within various further process steps (within the same or another process).

The steam utilization device (iv) can be any device known to a person skilled in the art as suitable for the inventive system and is preferably selected from an evaporator, a distillation device, a drying device, a heater/heating device for e.g. sterilizing vessels, a turbine for e.g. generating electricity or a nozzle.

In the following particularly preferred embodiments of the present invention are described and are not to be understood as limiting the invention in any respect.

Particularly Preferred Embodiment 1

Process for the production of chemical target compounds from lignocellulosic material, comprising the steps
  a) treating the lignocellulosic material by applying steam;
  b) separating the steam containing at least one chemical target compound from the treated lignocellulosic material;
  c) transferring the separated steam to a segregation device;
  d) segregating the phase containing the least one chemical target compound from the steam;
  e) subjecting the steam to a utilization step;
wherein the segregating according to step d) is carried out by use of a rectification column and wherein it is particularly preferred that the segregated phase containing the at least one chemical target compound is further transferred from the rectification column to a steam transformation device for condensation and a subsequent decanter. It is thereby particularly preferred that the decanted phase not containing the at least one chemical target compound is recycled to the rectification column and thus can be further purified (removal of remaining traces of the at least one chemical target compound). The treating of the lignocellulosic material according to step a) is preferably carried out by steam explosion.

Particularly Preferred Embodiment 2

Process as described according to preferred embodiment 1, further comprising the steps
  f) condensing the utilized steam of step e).
    and/or
  g) recycling of the condensed steam of step f) to step a) of the process.

Particularly Preferred Embodiment 3

Process for the production of chemical target compounds from lignocellulosic material, comprising the steps
a) treating the cellulosic material by applying steam;
  b) separating the steam containing at least one chemical target compound from the treated cellulosic material;
  b1) subjecting the separated steam to a utilization step;
  c1) transferring the stream of the utilized steam to a segregation device;
  d1) segregating the phase containing the at least one chemical target compound from the stream of the utilized steam;
  g) recycling of the stream of step d1) to step a) of the process;
wherein the segregating according to step d1) is carried out by filtration such as nanofiltration or pervaporation by use of e.g. a polydimethylsiloxane (PDMS), silicone, polyurethaneurea (PUU) membrane or washing of the stream. The treating of the lignocellulosic material according to step a) is preferably carried out by steam explosion. It is thereby particularly preferred that the utilization of the separated steam will automatically involve condensation of the steam. In case the utilization will not lead to a condensation of the steam, within a preferred embodiment of the respective process variant, the steam will be transferred to a condenser before step c1).

Particularly Preferred Embodiment 4

System for conducting the process for the production of chemical target compounds from lignocellulosic material comprising
  (i) reactor for the treatment of the lignocellulosic material according to step a) of the inventive process;
  (ii) steam separation device for separating the steam containing at least one chemical target compound from the treated cellulosic material according to step b) of the inventive process;
  (iii) steam segregation device for segregating the phase containing the least one chemical target compound from the steam according to step d) of the inventive process;
  (iv) steam utilization device for steam energy utilization;
whereas the steam segregation device comprises three segments, such as a rectification column (first segment), a steam transformer (second segment) and a decanter (third segment).

EXAMPLES

The present invention is now described by the following examples and figures. The examples and figures are for illustrative purposes only and are not to be understood as limiting the invention.

FIG. 1 shows an exemplary system and respective process of the present invention.

Figure 2B:
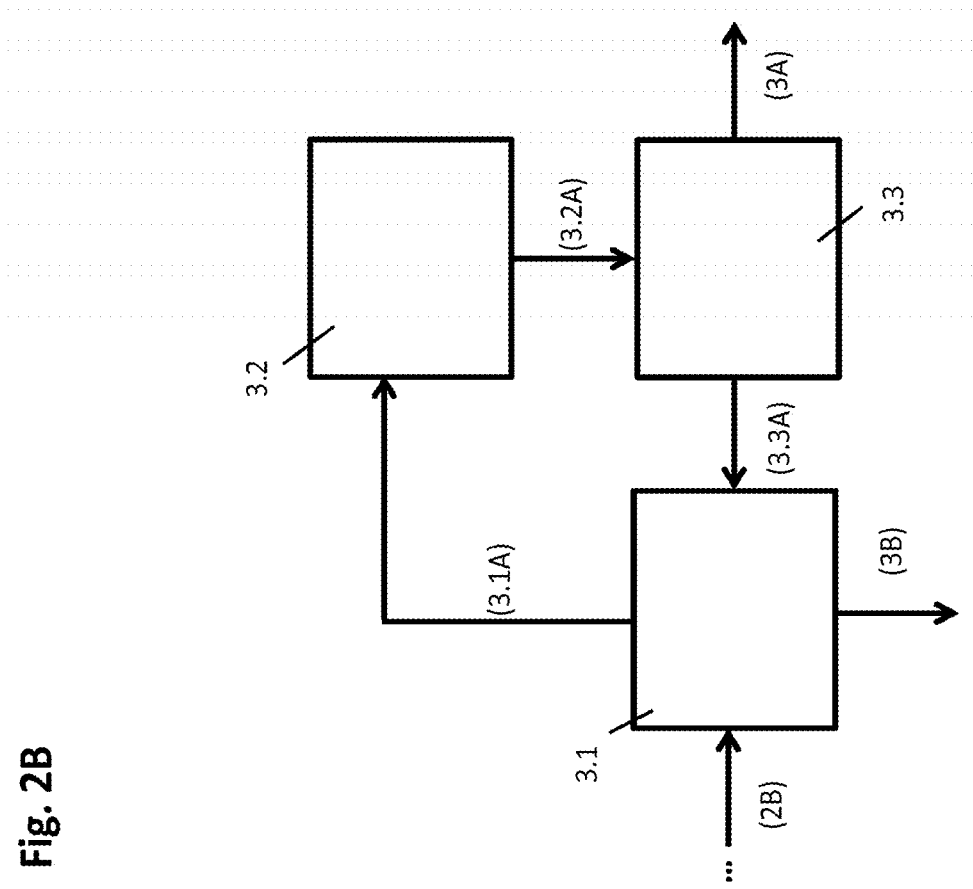
FIG. 2B shows a preferred embodiment of the segregation device (3). Within this preferred embodiment the segregation device (3) comprises three different segments such as a rectification column (first segment) (3.1), a steam transformer (second segment) (3.2) and a decanter (third segment) (3.3). Within this preferred embodiment, the stream (3.1A) comprising the at least one chemical target compound coming from the rectification column (3.1) is transferred to a condenser (3.2) such as e.g. a steam transformer and the condensed steam/process stream (3.2 A) coming from the condenser (3.2) is then transferred to a decanter (3.3) by which the phase/stream containing the at least one chemical target compound (3A) and the remaining watery stream (3.3A) are separated. Stream (3D) is then recycled to the rectification column (3.1).
Figure 2A:
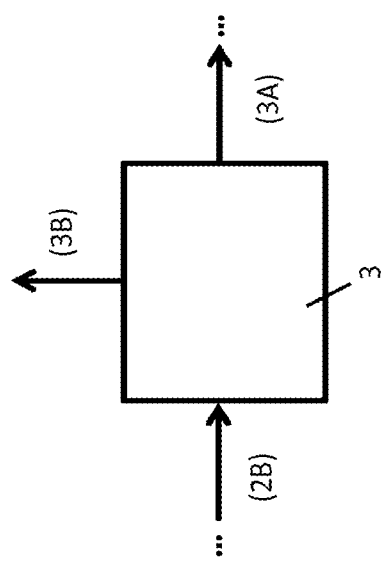
FIG. 2A shows the segregation device (3) and in- and out-going process streams: the steam process stream (2B) from the separation device, the outgoing process stream (3A) comprising the at least one chemical target compound and the outgoing process stream (3B) which constitutes the purified steam (steam depleted by the at least one chemical target compound).

FIG. 2A shows the segregation device and in- and outgoing process streams.

FIG. 2B shows a preferred embodiment of the segregation device and respective process-detail comprising three different segments.

Figure 3:
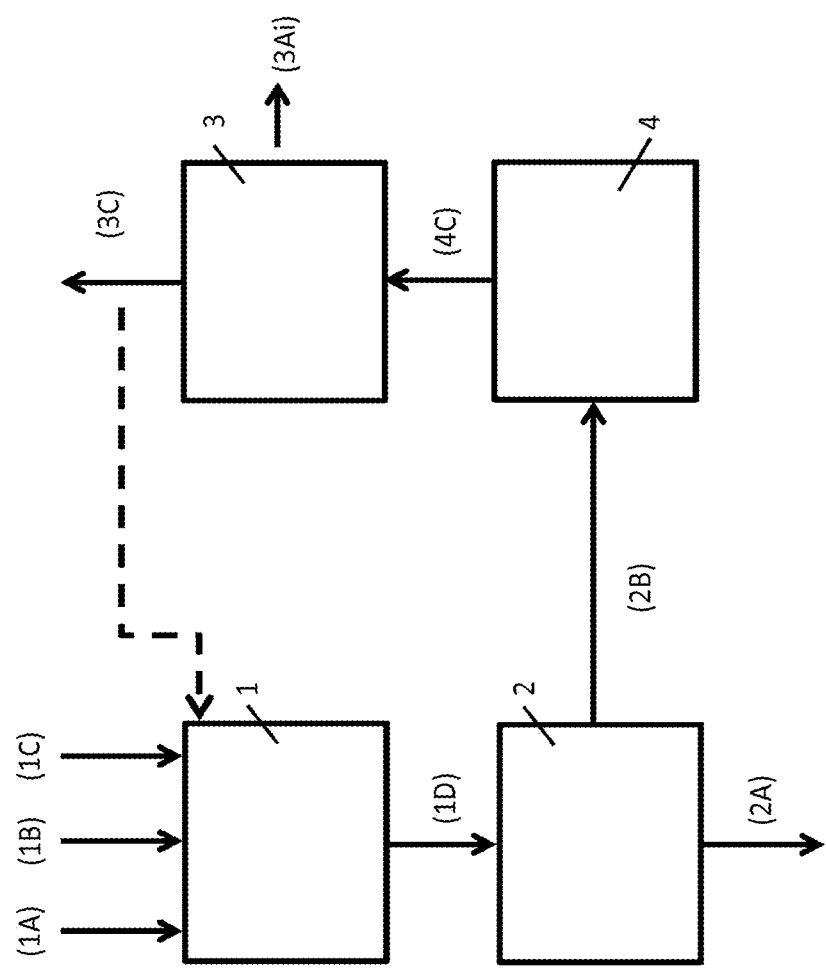
FIG. 3 illustrates a typical system for carrying out the process variant of the present invention wherein the treatment reactor (1) is fed by three process streams, the stream containing the cellulosic material (1A), the stream containing steam (1B) and the stream containing process water (1C) which may be recycled steam condensate from the steam utilization device (4). The steam-containing treated cellulosic material is then transferred by another process stream (1D) to a steam separation device (2). Two process streams emerge from the steam separation device (2), the stream of treated cellulosic material (2A) and the stream containing steam and the at least one chemical target compound (2B). The stream (2B) is then transferred to a steam utilization device (4). Within the steam utilization device (4), the steam condenses due to utilization and emerges as stream containing the at least one chemical target compound (4C). The stream containing the at least one chemical target compound (4C) is then transferred to the segregation device (3). Two process streams emerge from the segregation device (3), the stream containing the at least one chemical target compound in increased concentration (3Ai) and the purified watery stream (3C). The purified watery stream (3C) is then recycled to the treatment reactor (1) to be used as process water.

FIG. 3 shows an exemplary system and respective process of the process variant of the present invention.

Figure 4:
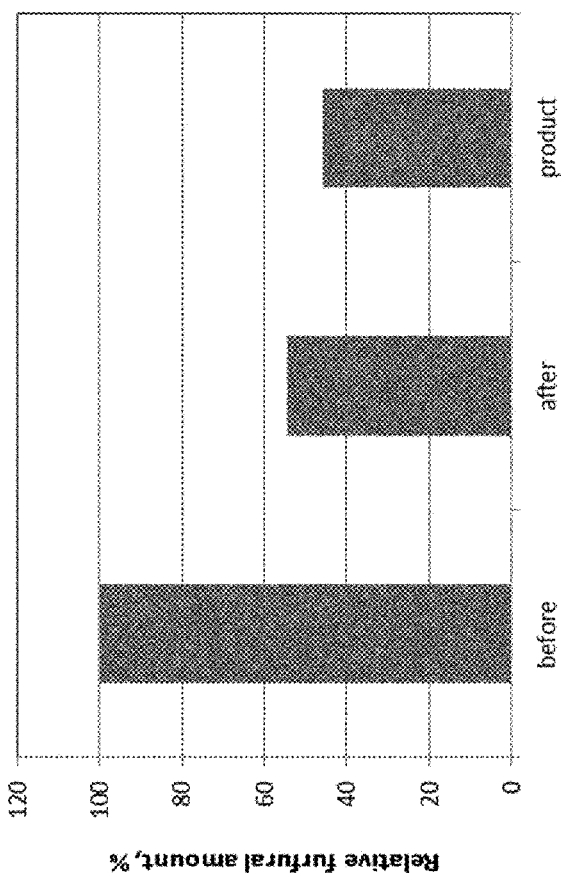
FIG. 4 shows the relative furfural content before and after adsorption as well as the furfural yield according to the inventive process as described within Example 1.

FIG. 4 shows the relative furfural content before and after adsorption as well as the furfural yield according to the inventive process as described within example 1

Example 1

Cereal straw with a dry matter content of 45% was treated by steam explosion (220° C.). The steam recovered during the pretreatment contained a certain amount of furfural. Furfural was recovered from the steam using an adsorption column (Gassner Glastechnik, Deutschland) as segregation device containing 500 g zeolite as adsorber material (ZSM-5, H-Form, $SiO_2/Al_2O_3=1000$; inert binding agent, producer: Clariant AG). To this aim, the steam was pumped through the adsorption column at a rate of 0.5 L/min for 5 h. The furfural content of the steam before and after the adsorption was determined by gas chromatography. The furfural content in the steam decreased to 54.3% thus resulting in a furfural yield of 45.7%. The results are shown within FIG. 4.

The invention claimed is:

1. A process for the production of chemical target compounds from cellulosic material comprising the steps
   a) treating cellulosic material by applying steam;
   b) separating the steam containing at least one chemical target compound from the treated cellulosic material;
   c) transferring the separated steam to a segregation device;
   d) segregating the phase containing the least one chemical target compound from the steam by rectification;
   e) subjecting the steam to a utilization step.

2. The process according to claim 1, wherein the segregation comprises steam transformation of the steam containing the at least one chemical target compound.

3. The process according to claim 2, wherein the segregation comprises decanting the phase containing the at least one chemical target compound from the transformed steam, resulting in said phase containing the at least one chemical target compound and a residual watery phase.

4. The process according to claim 3, wherein the residual watery phase is recycled to step d) after decanting the phase containing the at least one chemical target compound.

5. The process according to claim 1, wherein the utilization step e) is selected from evaporation, drying, heating, sterilizing, energy generating and distillation.

6. The process according to claim 1, further comprising the step
   f) condensing the utilized steam of step e).

7. The process according to claim 6, further comprising the step
   g) recycling of the utilized steam.

8. The process according to claim 7, wherein the utilized steam is recycled to step a) of the process.

9. The process according to claim 1, wherein the segregated chemical target compound according to step d) is one or more compounds selected from phenolic compounds, furans4-OH benzyl alcohol, 4-OH benzaldehyde, 4-OH benzoic acid, trimethyl benzaldehyde, 2-furoic acid, coumaric acid, ferulic acid, phenol, guaiacol, veratrole, pyrogallol, pyrogallol mono methyl ether, vanillyl alcohol, vanillin, isovanillin, vanillic acid, isovanillic acid, homovanillic acid, veratryl alcohol, veratraldehyde, veratric acid, 2-O-methyl gallic acid, syringyl alcohol, syringaldehyde, syringic acid, trimethyl gallic acid, homocatechol, ethyl vanillin, creosol, p-methyl anisol, anisaldehyde, anisic acid, furfural, hydroxymethylfurfural, 5-hydroxymethylfurfural, formic acid, acetic acid, levulinic acid, cinnamic acid, coniferyl aldehyde, isoeugenol, hydroquinone and eugenol.

* * * * *